United States Patent [19]

Hansen

[11] Patent Number: 4,480,929
[45] Date of Patent: Nov. 6, 1984

[54] METHOD AND A DEVICE FOR MEASURING CONCRETE MATURITY

[76] Inventor: Anker J. Hansen, Jaegervej 11, DK-2791 Dragor, Denmark

[21] Appl. No.: 410,970

[22] Filed: Aug. 24, 1982

[30] Foreign Application Priority Data

Aug. 28, 1981 [DK] Denmark ............................. 3818/81

[51] Int. Cl.$^3$ ............................................. G01N 25/00
[52] U.S. Cl. ....................................... 374/53; 374/54; 73/61.3; 73/73
[58] Field of Search .......................... 73/61.3, 803, 78; 374/53, 54

[56] References Cited

FOREIGN PATENT DOCUMENTS 70373 2/1973 Denmark .

OTHER PUBLICATIONS

Hansen, Anker Jon, "COMA-Meter-The Mini Maturity Meter", Sartryck ur Nordisk Betong, 4:81.

Catalog M-82 of Germann Petersen Manufacturing ApS.

Primary Examiner—Charles Frankfort
Assistant Examiner—Willie Morris Worth
Attorney, Agent, or Firm—Lewis H. Eslinger

[57] ABSTRACT

A method and a device for measuring the maturity of concrete, in which the heat generated by the setting of the concrete causes a special liquid to evaporate and the amount of evaporated liquid is taken as a measure of the concrete maturity. The liquid is contained in a closed capillary tube placed on a scale. For measuring purposes the capillary tube is broken at a well-defined point, and capillary and scale are then placed in a casing containing an absorbing agent for the evaporated liquid. The casing is hermetically sealed and pressed into the concrete. For reading purposes the casing is opened and the scale with the capillary is removed to determine the level of the liquid column and thus the maturity of the concrete.

3 Claims, 2 Drawing Figures

METHOD AND A DEVICE FOR MEASURING CONCRETE MATURITY

The invention relates to a method of measuring the maturity of concrete, in which a liquid is heated by means of the heat generated by the setting of the concrete and the evaporated amount of liquid is taken as a measure of the maturity of the concrete.

The invention also relates to a device for carrying out the method of the invention.

Hardening of concrete is a chemical process, the rate of which depends upon the temperature. Therefore, the hardening process can be monitored by recording the temperature in the period after casting. Concrete maturity is often calculated as the product of temperature and time. The strength of a given concrete can be determined by means of a calibration curve once the order of maturity is known. Maturity can either be stated in degrees x time or in time (days) in which the concrete has had a reference temperature (generally 20° C.).

As hardening of concrete is a chemical process, the maturity can more correctly be described by the Arrhenius equation for thermally activated processes:

$$\text{maturity} = K \exp\left(-\frac{E}{RT}\right)$$

where E is the activation energy for the process (the ease with which an increase in the temperature increases the rate of the process), R is the gas constant, T the temperature in Kelvin, and K a proportionality constant. This equation implies that the maturity of a concrete which has had a temperature of 20° C. for two days is less than that of a concrete which has had a temperature of 40° C. for one day. Thus, there is no linear proportionality between maturity and temperature, as is presupposed in most methods of maturity determination. The maturity as determined by the above-mentioned formula gives a more correct measure of the strength of concrete.

The previous methods of concrete maturity determination are all based on recording of temperature:

(1) Reading of the temperature of the concrete by means of a thermometer at different moments for a given period of time, and calculation of maturity on the basis of tabulated values.

(2) Continuous recording of the temperature by a probe and current calculation of maturity by a computer.

These methods of maturity determination suffer from the drawback that maturity cannot be read directly, but has to be calculated on the basis of collected data, or they are electronic and thus expensive and delicate.

The vapour pressure of a liquid increases with increasing temperature, as appears from the Arrhenius equation (vapour pressure being substituted for maturity). Since the evaporation is proportional with the vapour pressure, maturity can be determined directly as the amount of evaporated liquid when E (activation energy) for the vapour pressure of the liquid is of the same order as E for the concrete hardening.

The Danish Patent Application No. 703/33 describes a device for use in the determination of concrete maturity. This device relies on the evaporation of a liquid as the basis for the measurement, which is performed by reading the amount of liquid that evaporates from a reservoir communicating with a plurality of interconnected containers.

This construction of the instrument, however, is inexpedient. Firstly, the evaporation reservoir has to be directly connected to the ambient air in order to enable the liquid to evaporate constantly and the air to penetrate into the other containers. This causes the rate of evaporation to be influenced by the weather conditions, in particular the wind. Secondly, the instrument can be used in only one position (horizontal), because otherwise the depletion rate of the interconnected containers would change as a consequence of the influence of gravitation.

The method of the present invention is characterized in that a liquid with an activation energy for vapour pressure of approximately the same value as the activation energy for concrete hardening is contained in an open capillary tube fitted in a closed container to be placed in the concrete, said container containing an absorbing agent which absorbs the vapours developed by the evaporation of the liquid.

As mentioned, the liquid contained in the capillary tube must have an activation energy for vapour pressure of approximately the same value as the activation energy for concrete hardening. This activation energy is about 40 kJ/mole for ordinary concrete. Usually only non-polar liquids have sufficiently low activation energies for vapour pressure. In practice liquids will be selected which are non-inflammable, non-toxic and shelf-stable, e.g. are not decomposed when exposed to light. For example, some halogenated hydrocarbons possess these characteristics, and liquids which have been found to be useful include 1-bromo-1-chloroethane, 1,1,1-trichloroethane and 1-bromobutane. A suitable absorbing agent for such liquids is active carbon.

An embodiment of a device for carrying out the invention is illustrated in the drawings.

Figure 1:
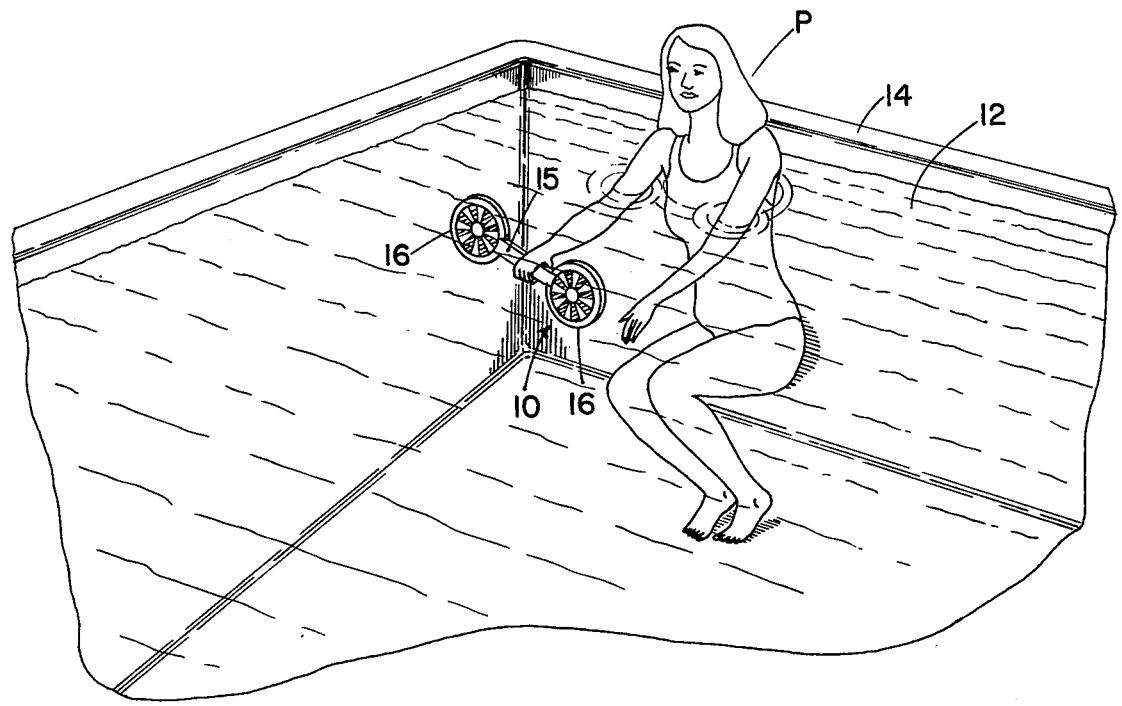
FIG. 1 shows a device for measuring the maturity of concrete in accordance with the present invention.

The device for carrying out the method of the invention is characterized in that the container is an open capillary tube containing a liquid with an activation energy for vapour pressure of approximately the same value as the activation energy for concrete hardening, the capillary tube being fitted in a closed container containing a substance which absorbs the vapours developed by the evaporation of the liquid.

The device, as supplied, comprises a closed capillary containing the specified liquid; the capillary is opened immediately before the maturity measurement. The capillary is fitted in a closed container containing an absorbing agent for the vapours developed by the evaporation of the liquid.

Compared to the above-mentioned known method, the unique feature of the present invention is that the metering liquid evaporates in a closed chamber so that only the concrete and not the surrounding affect the evaporation rate. The device of the invention can therefore be used submerged in water.

The device can expediently be constructed as a closed capillary tube, filled with the specific liquid and placed on a scale. When the measurement is to be started, the capillary tube is broken at a well-defined point, and capillary and scale are then placed in a casing containing a vapour absorbing substance. The casing is hermetically sealed and then pressed into the concrete at the desired metering point. To measure maturity, the casing is opened and the scale with the capillary is removed for reading the level of the liquid in the capillary. The height of the liquid column currently shows the maturity of the concrete.

EXAMPLE

Active carbon 7 as the vapour absorbing substance is placed at the bottom of a casing formed as a test tube 5. At the start of the test, the test tube is pressed down into the concrete 8, and a scale 3, which mounts an open capillary 1 filled with 1-bromo-1-chloro-ethane, is placed in the tube, which is then sealed with a plug 6. For reading purposes, the test tube is opened and the height of the liquid in the capillary is read using the scale 3.

I claim:

1. A method of determining the maturity of concrete, in which a liquid is heated by means of the heat generated by the setting of the concrete and the evaporated amount of liquid is taken as a measure of the concrete maturity, characterized in that a liquid with an activation energy for vapour pressure of approximately the same value as the activation energy for concrete hardening is contained in an open capillary tube fitted in a closed container to be placed in the concrete, said container containing an absorbing agent which absorbs the vapours developed by the evaporation of the liquid.

2. A method according to claim 1, characterized in that the liquid contained in the capillary tube is selected from the group consisting of 1-bromo-1-chloroethane, 1,1,1-trichloroethane and 1-bromobutane and that the absorbing agent is active carbon.

3. A device for carrying out the method as claimed in claim 1 or 2 for determining the maturity of concrete, said device comprising a container for liquid, the evaporation of which is taken as a measure of the concrete maturity, characterized in that the container is an open capillary tube containing a liquid with an activation energy for vapour pressure of approximately the same value as the activation energy for concrete hardening, the capillary tube being fitted in a closed container containing a substance which absorbs the vapours developed by the evaporation of the liquid.

* * * * *

UNITED STATES PATENT AND TRADEMARK OFFICE
CERTIFICATE OF CORRECTION

PATENT NO. : 4,480,929

DATED : November 6, 1984

INVENTOR(S) : Anker J. Hansen

It is certified that error appears in the above-identified patent and that said Letters Patent is hereby corrected as shown below:

In the GRANT ONLY, delete the sheet of drawings bearing Patent No. 4,480,829 and insert the sheet of drawings as shown on the attached page.

Column 1, line 64, "703/33" should read --703/73--.
Column 2, line 60, "surrounding" should read --surroundings--.

*Signed and Sealed this*

*Twenty-fourth* Day of *September 1985*

[SEAL]

*Attest:*

DONALD J. QUIGG

*Attesting Officer*

*Commissioner of Patents and Trademarks—Designate*

Figure 2:
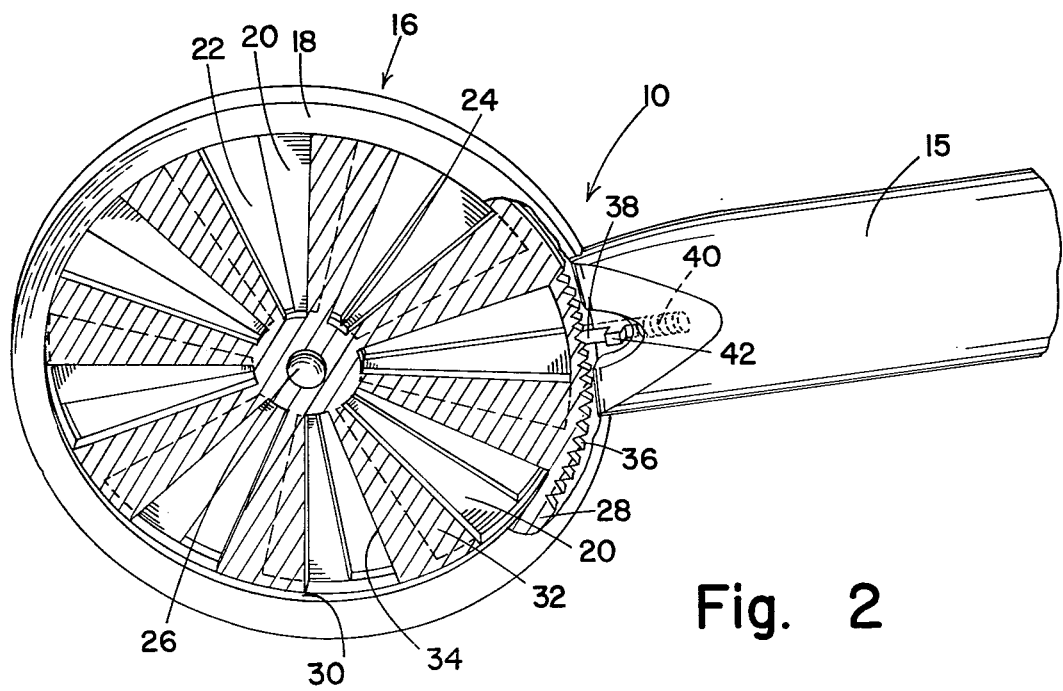
FIG. 2 shows the device illustrated in FIG. 1 embedded in concrete.

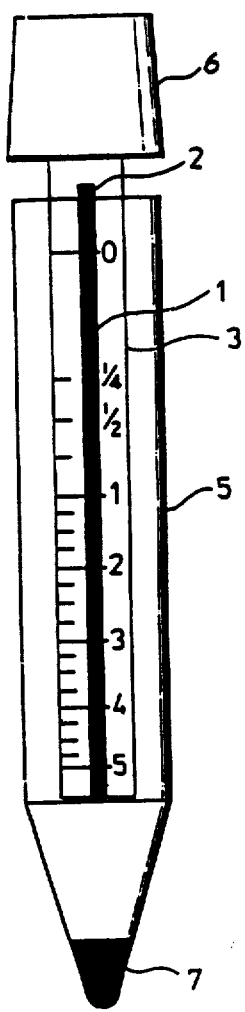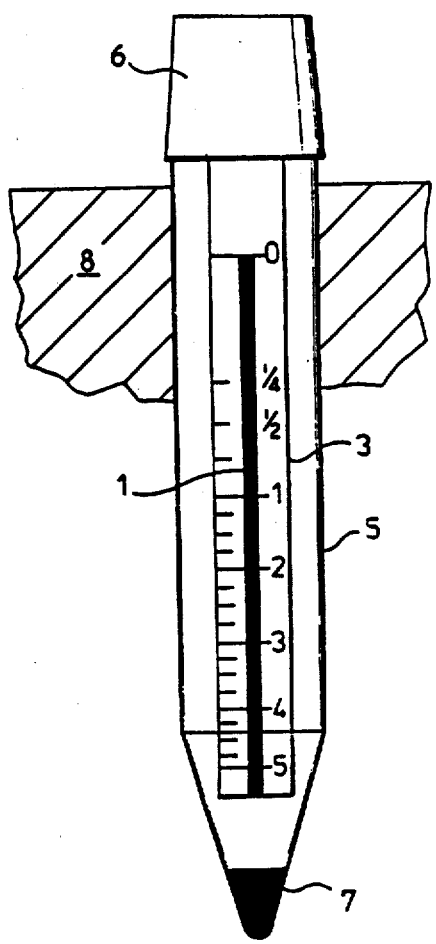
FIG. 1.
FIG. 2.